(12) United States Patent
Montani et al.

(10) Patent No.: US 12,098,014 B2
(45) Date of Patent: Sep. 24, 2024

(54) COMPOUND MATERIAL, CONTAINER AND STERILE PRODUCT

(71) Applicant: S.M.P. S.R.L., Airuno (IT)

(72) Inventors: Fiorenzo Montani, Airuno (IT); Diego Stucchi, Airuno (IT)

(73) Assignee: S.M.P. S.R.L., Airuno (IT)

( * ) Notice: Subject to any disclaimer, the term of this patent is extended or adjusted under 35 U.S.C. 154(b) by 130 days.

(21) Appl. No.: 17/417,342

(22) PCT Filed: Dec. 23, 2019

(86) PCT No.: PCT/IB2019/061295
§ 371 (c)(1),
(2) Date: Jun. 22, 2021

(87) PCT Pub. No.: WO2020/136556
PCT Pub. Date: Jul. 2, 2020

(65) Prior Publication Data
US 2022/0073255 A1   Mar. 10, 2022

(30) Foreign Application Priority Data
Dec. 27, 2018   (IT) .......................... 102018000021265

(51) Int. Cl.
*B65D 81/24*   (2006.01)
*B32B 1/00*   (2006.01)
(Continued)

(52) U.S. Cl.
CPC ................ *B65D 81/24* (2013.01); *B32B 1/00* (2013.01); *B32B 19/02* (2013.01); *B32B 27/00* (2013.01);
(Continued)

(58) Field of Classification Search
CPC ........ B65D 81/24; B65D 1/0207; B32B 1/00; B32B 19/02; B32B 27/00; B32B 27/08;
(Continued)

(56) References Cited

U.S. PATENT DOCUMENTS 4,775,585 A   10/1988   Hagiwara et al.
4,911,898 A   3/1990   Hagiwara et al.
(Continued)

FOREIGN PATENT DOCUMENTS

EP   2394931 A1   12/2011
WO   WO 00/38552 A1   7/2000

*Primary Examiner* — James C Yager
(74) *Attorney, Agent, or Firm* — James S. Keddie; Bozicevic, Field & Francis LLP

(57) ABSTRACT

Sterile container (1) comprising a container body (40) having inner surfaces (2, 4) delimiting a containment compartment (6), wherein at least part of said surfaces (2, 4) is made of a compound material comprising a thermoplastic polymer, a first zeolite and a second zeolite homogeneously dispersed in the thermoplastic polymer, each of said zeolites having a micrometric particle size distribution and delimiting reticular voids in which bactericidal and/or bacteriostatic metal ions releasable from said zeolite are housed. The first zeolite comprises silver and copper metal ions, the second zeolite comprises silver and zinc metal ions. The present invention further relates to a sterile product and a compound material.

13 Claims, 5 Drawing Sheets

(51) Int. Cl.
*B32B 19/02* (2006.01)
*B32B 27/00* (2006.01)
*B32B 27/08* (2006.01)
*B32B 27/30* (2006.01)
*B32B 27/32* (2006.01)
*B65D 1/02* (2006.01)

(52) U.S. Cl.
CPC ............ *B32B 27/08* (2013.01); *B32B 27/306* (2013.01); *B32B 27/32* (2013.01); *B65D 1/0207* (2013.01); *B32B 2250/40* (2013.01); *B32B 2264/10* (2013.01); *B32B 2264/102* (2013.01); *B32B 2264/2031* (2020.08); *B32B 2307/7242* (2013.01); *B32B 2307/7244* (2013.01); *B32B 2307/7246* (2013.01); *B32B 2439/60* (2013.01); *Y10T 428/1352* (2015.01); *Y10T 428/1379* (2015.01); *Y10T 428/1383* (2015.01)

(58) Field of Classification Search
CPC ... B32B 27/306; B32B 27/32; B32B 2250/40; B32B 2264/10; B32B 2264/102; B32B 2264/2031; B32B 2307/7242; B32B 2307/7244; B32B 2307/7246; B32B 2439/60; Y10T 428/1352; Y10T 428/1379; Y10T 428/1383; A61L 2202/182; A61L 2/238; A61L 12/086; A61L 12/088; A01N 59/16; A01N 25/34; A61F 9/0008

See application file for complete search history.

(56) References Cited

U.S. PATENT DOCUMENTS

| | | | |
|---|---|---|---|
| 4,938,955 A | | 7/1990 | Niira et al. |
| 5,003,638 A | | 4/1991 | Miyake et al. |
| 5,320,843 A | * | 6/1994 | Raheja ................. A61L 12/088 206/524.4 |
| 5,899,361 A | * | 5/1999 | Durliat ............... B65D 81/3227 D9/450 |
| 2002/0018732 A1 | * | 2/2002 | Hung ...................... A61L 12/14 422/28 |
| 2003/0118658 A1 | | 6/2003 | Trogolo et al. |

* cited by examiner

COMPOUND MATERIAL, CONTAINER AND STERILE PRODUCT

CROSS-REFERENCE TO RELATED APPLICATIONS

This application is a § 371 national phase of International Application No. PCT/IB2019/061295, filed on Dec. 23, 2019, which claims the benefit of Italian Application No. 102018000021265, filed on Dec. 27, 2018, all of which applications are incorporated by reference herein.

The present invention regards a compound material characterised by an effective antibacterial and/or bacteriostatic action, as well as fungicidal action, a sterile or sterilised container and a sterile product comprising such material.

A closable container comprising a polymeric material containing silver and zinc in ionic form, associated with a solid support, is known from the prior document EP 2 394 931 A1 of the same proprietor.

One of the drawbacks of the material used in the prior art lies in the failure to comply with the European Pharmacopoeia (PhEur) reference standards, which is the code identifying common, harmonised and homologous standards for the quality of national medicines at European level.

According to such code, certain uses of the pharmaceutical preparations (for example in the ophthalmic industry) not only require an antibacterial stability of the preparations contained in the containers of the aforementioned type, but also impose a stability as concerns the growth and proliferation of the fungi after the container is opened for the first time. As a matter of fact, although said containers are usually sterilised, filled with sterile preparations and subsequently sealed, it is inevitable that sterility conditions will be lost after the container is opened for the first time. Nevertheless, containers complying with the aforementioned standard must be able to prevent growth and proliferation of fungi or bacteria for a predetermined period of time of use of said container and the content thereof, during which the container is opened and closed several times.

Thus, the present invention falls within the context outlined above, setting out to provide an improved container and product, capable of overcoming the strict requirements of the aforementioned standard, said container being in particular capable of maintaining (i.e. not decreasing) the level of sterility inside, and preferably also outside said container.

Without aiming at providing a scientific explanation of the phenomenon, the inventors of the present invention theorised that a selection of specific metal ions with antibacterial and/or bacteriostatic function, distributed homogeneously on the surface to a polymeric matrix, and supported on a zeolite in micrometric form, also allow to obtain an improved fungicidal effect with respect to the solutions of the prior art.

This objective is achieved by means of a sterile container, by means of a sterile product, and by means of a compound material.

The subject of the present invention will now be illustrated based on the attached drawings, provided by way of non-limiting example, wherein.

Figure 1:
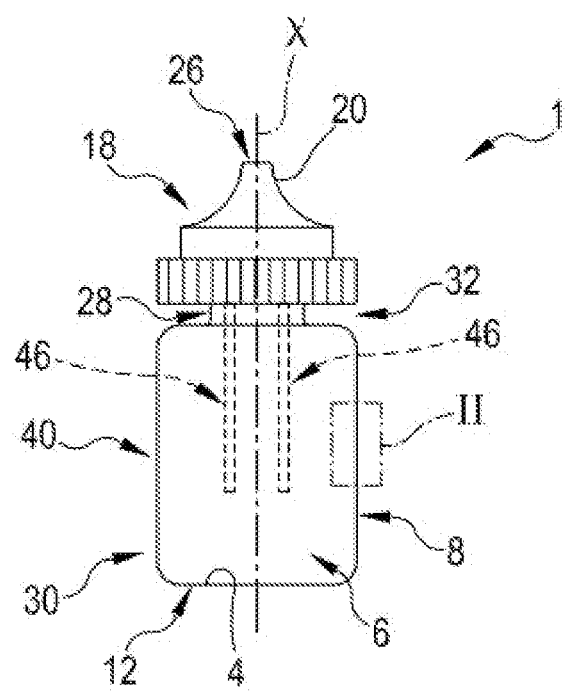
FIG. 1 shows a schematic lateral view of a container, subject of the present invention, according to a possible embodiment.

With reference to the aforementioned drawings, the reference number 1 denotes a sterile container in its entirety, and the reference number 10 denotes a sterile product.

According to an embodiment, the sterile container 1 is a tray or a container in particular for contact lenses, a bottle, a phial or the like.

The sterile container 1 comprises a container body 40 having inner surfaces 2, 4 which delimit a containment compartment 6, in particular suitable for containing a solution, a liquid or a preparation. In the following description, the solution, the liquid or the preparation will sometimes be defined as the "content" of the containment compartment.

It should be noted that, in this description, the expression "inner surface" is used to indicate a surface arranged in and/or facing the containment compartment 6. Therefore, the inner surfaces could be the inner surfaces 2, 4 (specifically of the lateral wall 8 and/or of the bottom wall 12) which delimit a volume of said compartment 6, or other surfaces inside the containment compartment 6 which delimit only a part thereof. By way of example, in the present description, the expression "inner surfaces" shall also be understood as at least partly circumscribing (for example: completely) one or more ion exchange elements 46 projecting into the housing compartment 6. The ion exchange elements 46 will be described in more detail hereinafter.

In the embodiments shown, the container body 40 comprises a lateral wall 8 which extends in a tubular or conical manner around a main extension axis X. Therefore, the lateral wall 8 radially circumscribes the containment compartment 6.

It should be observed that, in the present description, the expressions "radial", "axial", "orthogonal", or "coaxial" shall always refer to the main extension axis X, unless otherwise specified. Optionally, the container body 40 comprises a bottom wall 12 which delimits on one side the containment compartment 6, precisely at a first axial end 30 of the container body 40.

According to an embodiment, the bottom wall 12 extends in a substantially orthogonal manner with respect to the main extension axis X, and advantageously with respect to the lateral wall 8.

According to a variant, the inner surfaces 2, 4 are at least partly delimited by the lateral wall 8 and/or by the bottom wall 12.

Optionally, the bottom wall 12 could be connected to the lateral wall 8, for example being obtained as a single piece with the latter.

According to an embodiment, the lateral wall 8 and the bottom wall 12 could be made at least partly made of the same material.

At least part of the inner surfaces 2, 4 is made of a compound material comprising a thermoplastic polymer, a first zeolite and a second zeolite.

According to one embodiment, the thermoplastic polymer comprises or consists of polyethylene, specifically high-density polyethylene, medium density polyethylene or low-density polyethylene.

According to other embodiments, the thermoplastic polymer is selected from among the group consisting of polypropylene (PP), polyethylene terephthalate (PET), PET-G (i.e. polyethylene terephthalate glycol-modified), polyvinyl chloride (PVC), polycarbonate (PC), polybutadiene-styrene (PBS), acrylonitrile-butadiene-styrene (ABS), polyacetal (POM) resin, acrylic resins, polyamide, nylon (for example nylon 6 or nylon 66), derivatives thereof, and mixtures thereof.

According to an embodiment, the container body 40 (for example: the lateral wall 8 and/or the bottom wall 12) is integrally made of only one material from among those mentioned in this description. More precisely, the container body could be obtained with full thickness (that is, from an inner surface 2 to an outer surface 22 of the container body 40) using the compound material subject of the present invention which comprises the thermoplastic polymer, the first zeolite and the second zeolite.

According to another embodiment, the container body 40 (for example: the lateral wall 8 and/or the bottom wall 12) could be made of several layers of different type.

For example, the container body 40, or the lateral wall 8 and/or the bottom wall 12, could comprise an inner layer 14, an optional intermediate layer 48 (better to say: one or more intermediate layers) and an outer layer 16. In particular, these layers could be arranged in this order from the containment compartment 6 ("from the inside") toward the outside.

The first zeolite and the second zeolite are advantageously dispersed homogeneously in the thermoplastic polymer.

Thus, at least a part of the zeolites is incorporated in the thermoplastic polymer, while another part of such zeolites is arranged in a surface position.

Specifically, at least one part of the first and second zeolites is arranged at the inner surfaces 2, 4.

According to a manufacturing variant, the incorporation or dispersion of zeolites in the thermoplastic polymer could occur when the latter is in an at least partially softened or molten state (for example, after heating).

According to one embodiment, the first and/or second zeolite comprise or consist of a synthetic zeolite.

For example, such zeolite could be selected from among the group consisting of zeolite A, zeolite X, zeolite Y, zeolite T and mixtures thereof.

According to another embodiment, the first and/or second zeolite comprise or consist of a natural zeolite. For example, such zeolite could be selected from among the group consisting of sodalite, mordenite, analcite, clinoptilolite, chabazite, erionite and mixtures thereof.

Advantageously, the first and second zeolite comprise, or consist of, the zeolite (for example natural or synthetic).

According to a variant, the granules or particles of the first and/or of the second zeolite are non-deformable (i.e. they do not have structural elasticity).

Furthermore, each of the aforementioned zeolites has a micrometric particle size distribution, and it delimits reticular voids in which bactericidal and/or bacteriostatic metal ions releasable from such zeolite are housed.

Therefore, the described zeolites act as a support for the bactericidal and/or bacteriostatic metal ions, with respect to which the ions can be released under the conditions described below.

As regards a possible method for manufacturing the first and/or second zeolite containing the bactericidal and/or bacteriostatic metal ions, reference shall be made, for example—mutatis mutandis—to the description of the prior art document n° U.S. Pat. No. 4,775,585. Specifically, in the examples ("Example for reference") from 1 to 3—from column 10 at the bottom to column 12 to the bottom—show how to arrange silver ions, copper ions and zinc ions in zeolites, by means of ion exchange in aqueous solutions containing salts of such ions.

As regards the terminology used in the present description, the expression "micrometric particle size distribution" is used to indicate a distribution of the sizes of the zeolite particles comprised in the range from 0.1-800 µm, optionally 0.1-400 µm, advantageously 0.1-100 µm.

According to other embodiments, the particle size distribution could be less than 50 µm, optionally less than 25 µm, advantageously less than 15 µm.

Solely by way of example, the particle size distribution could be in comprised in the range from 0.1-12 µm, optionally 0.1-9 µm.

The expression "bactericidal and/or bacteriostatic metal ions" is used to indicate metal ions capable of reducing bacterial populations, or even solely suitable to prevent an increase or proliferation of such populations. Embodiments of the metal ions used for this purpose include silver ions, zinc ions, copper ions and mixtures thereof. According to a variant gold ions or other metal ions could also be present, for example with a co-adjuvant function for the other ions.

On the other hand, the expression "releasable" is used to indicate a capacity or attitude of the bactericidal and/or bacteriostatic metal ions to emerge from the reticular voids delimited by the zeolite (in particular, by the crystal lattice thereof) to which they are associated, and by which they are supported.

More precisely, such release (or ion exchange) occurs in a liquid, advantageously in an aqueous solution, specifically in the presence of other ions—for example ions of at least one alkaline metal—capable of replacing the bactericidal and/or bacteriostatic metal ions inside the zeolite lattice.

According to an advantageous embodiment, the first and/or second zeolite contain bactericidal and/or bacteriostatic metal ions, which are housed in the lattice of zeolites, for example in interstitial position.

According to a further embodiment, the first and/or second zeolite has an apparent density or bulk density comprised in the range from 0.45-0.65 g/cm$^3$, optionally 0.45-0.55 g/cm$^3$, for example 0.48-0.52 g/cm$^3$.

According to the invention, the first zeolite comprises silver and copper metal ions, the second zeolite comprises silver and zinc metal ions.

In other words, more than one type of bactericidal and/or bacteriostatic metal ion is associated with each zeolite.

Unexpectedly, such accurate selection of ions associated with the other expedients described above allows to obtain a drastically improved fungicidal action with respect to the solutions of the prior art.

By way of example, the first zeolite could comprise or consist of the AGION® product, product code AK 10D, marketed by Sciessent LLC (Wakefield, MA 01880).

By way of further example, the second zeolite could comprise or consist of the AGION® product, product code AC10N or AC10D or AC10H, marketed by Sciessent LLC (Wakefield, MA 01880).

According to an embodiment, said container—filled with 10 ml of phosphate-buffered saline solution and subjected to a temperature of 60° C. for 10 days—releases bactericidal and/or bacteriostatic metal ions from said zeolites at the following amounts: silver <1.00 µg, copper 7.00 µg, zinc 17.00 µg.

According to a second embodiment, said container—filled with 10 ml of a sodium chloride solution (at 0.9% by weight with respect to the total weight of said solution) and subjected to a temperature of 60° C. for 10 days—releases bactericidal and/or bacteriostatic metal ions from said zeolites at the following amounts: silver 0.005 μg, copper 0.005 μg, zinc 0.027 μg.

According to an extremely advantageous embodiment, the following relation is valid in the compound material:

$$0.05<(Ag1+Ag2)/(Cu1+Zn2)<0.8$$

wherein:
Ag1 is the percentage by weight (% wt) of the silver ions with respect to the weight of the first zeolite;
Ag2 is the percentage by weight (% wt) of the silver ions with respect to the weight of the second zeolite;
Cu1 is the percentage by weight (% wt) of the copper ions with respect to the weight of the first zeolite;
Zn2 is the percentage by weight (% wt) of the zinc ions with respect to the weight of the second zeolite;

Therefore, this relation well exemplifies how the silver ion may be present at a lower amount with respect to the other two ions.

According to another embodiment, one of the following relations is valid:

$$0.05<(Ag1+Ag2)/(Cu1+Zn2)<0.55$$

or $$0.05<(Ag1+Ag2)/(Cu1+Zn2)<0.35$$

wherein the meaning of symbols Ag1, Ag2, Cu1, Zn2 is the same as that discussed above.

It should be observed that, unless otherwise specified, the percentages given in this description are percentages by weight (% wt).

According to a variant embodiment, the percentage by weight of the silver ions with respect to the weight of the first zeolite (Ag1) is comprised in the range from 2-5%.

According to a further embodiment, the percentage by weight of the silver ions with respect to the weight of the second zeolite (Ag2) is comprised in the range from 4.3-5.5%.

According to an even further embodiment, the percentage by weight of the copper ions with respect to the weight of the first zeolite (Cu1) is comprised in the range from 4-7%.

According to another variant embodiment, the percentage by weight of the zinc ions with respect to the weight of the second zeolite (Zn2) is comprised in the range from 12-16%, for example being about 14%.

According to an advantageous embodiment, the compound material comprises—per 100 grams of thermoplastic polymer (or better to say: every 100 grams of such polymer)—an amount of first zeolite equal to or greater than 5%, preferably equal to or greater than 5.5%, and an amount of second zeolite equal to or greater than 5%, preferably equal to or greater than 5.5%, with respect to the total weight of said compound material.

According to another advantageous embodiment, the compound material comprises—per 100 grams of thermoplastic polymer (or, better: every 100 grams of such polymer)—an amount of first zeolite equal to or lesser than 15% by weight, preferably equal to or lesser than 10% by weight, and an amount of second zeolite equal to or lesser than 15% by weight, preferably equal to or lesser than 10% by weight.

Preferably, the compound material comprises—per 100 grams of thermoplastic polymer (or better to say: every 100 grams of such polymer)—an amount of first zeolite comprised from 5.5% by weight to 10% by weight), preferably comprised from 5.8% by weight to 9% by weight, even more preferably comprised from 6% by weight to 8.5% by weight, and an amount of second zeolite comprised from 5.5% by weight to 10% by weight, preferably comprised from 5.8% by weight to 9% by weight, even more preferably comprised from 6% by weight to 8.5% by weight, with respect to the total weight of said compound material.

By way of example, each amount of zeolite (first and second) could be about 6-8.5% by weight per (or: every) 100 grams of thermoplastic polymer.

According to a variant embodiment, the container body 40 (for example: the lateral wall 8 and/or the bottom wall 12) could be wholly made of the present compound material, that is: thermoplastic polymer, first zeolite, second zeolite, each zeolite comprising the antibacterial and/or bacteriostatic metal ions defined herein as essential.

For embodiments that provide for a multilayer container body 40 (for example: a lateral wall 8 and/or a bottom wall 12), the inner layer 14 comprises, or consists of, the compound material discussed above. Advantageously, the outer layer 16 could be free of zeolites, and therefore free of bactericidal and/or bacteriostatic metal ions.

Figure 2A:
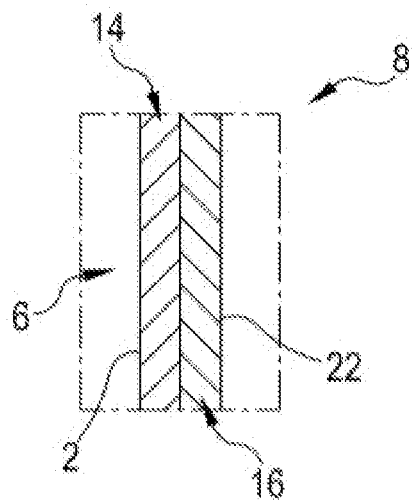
FIG. 2A is a sectional view of the area Il shown in FIG. 1, according to a possible embodiment.
Figure 2B:
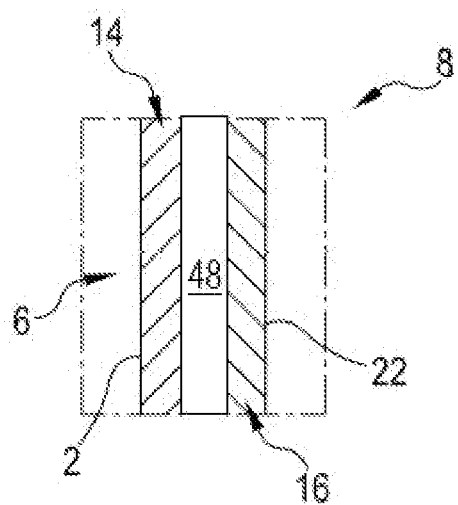
FIG. 2B is a sectional view of the area Il shown in FIG. 1, according to another possible embodiment.

Obviously, the expression "inner" is used to indicate the layer which at least partly delimits the, and faces the, containment compartment 6 and which is suitable to come into contact with the contents. This variant is for example schematised in FIG. 2, where the inner surface 2 is at least partly delimited (for example: completely) by the inner layer 14, while an outer surface 22 of the container body 40 could be at least partly (for example: completely) delimited by the outer layer 16.

By way of example, the thickness of the inner layer 14 could be about equal to the thickness of the outer layer 16.

By way of further example, the thickness of the inner layer 14 could be equal to or greater than about 20% of the thickness of the outer layer 16, for example about 20-70% of the thickness of the outer layer 16.

According to an advantageous variant, the inner layer 14 and the outer layer 16 could be in direct contact with each other (i.e. in the absence of intermediate layers).

Obviously, the function of the inner layer 14 according to such embodiments is to exert the antibacterial and/or bacteriostatic and fungicidal action with respect to the environment of the containment compartment, and to the content of the latter.

As regards the function of the outer layer 16, the latter could provide a protective layer for the inner layer, a reinforcing layer and/or a decorative or surface finishing layer.

For example, according to the latter variant, the outer layer could be at least partially (for example: completely) opaque, in order to hide at least part of the inner layer from view.

According to an embodiment, the outer layer 16 could be joined to the inner layer 14 as a single piece. In particular, this joining could be obtained by co-extrusion, co-moulding, co-injection or over-moulding.

Preferably, the outer layer 16 could be at least partially (for example: completely) made of a recycled thermoplastic polymer, more preferably recycled low-density polyethylene, recycled medium density polyethylene or recycled high density polyethylene, even more preferably recycled low-density polyethylene.

More preferably, said recycled thermoplastic polymer comprises an amount of recycled polymer comprised between 1% and 100% by weight, preferably comprised from 20% to 70% by weight, even more preferably comprised between 40% and 60% by weight, the possible residual amount being made of thermoplastic polymer obtained from first polymerisation.

The outer layer 16 is preferably made of a bio-based thermoplastic polymer at a percentage equal to or greater than 90% by weight (determined using the ASTM D6866 method in force at the date of filing of the present patent application), preferably comprised from 90% to 100% by weight, more preferably comprised from 93% to 99.8% by weight, even more preferably comprised from 95% to 99.5% by weight. Preferably, the bio-based thermoplastic polymer is polyethylene, more preferably low-density polyethylene. More preferably, the low density, bio-based polyethylene has a melt flow index (MFI; 190° C./2.16 kg)—determined by means of ASTM D 1238—comprised from 0.55 g/10 min to about 0.65 g/10 min (preferably about 0.60 g/10 min), and a density—determined by means of ASTM D 1505—comprised from 0.900 g/cm3 to 0.950 g/cm3 (preferably about 0.924 g/cm3). Even more preferably, the bio-based low-density polyethylene has the following characteristics (relative to a blown film with a thickness of 40 μm in an extruder with a diameter of 50 mm with a 2.2:1 blowing ratio, and with a 1 mm head light):

| Feature | Method of measurement | Units | Values |
|---|---|---|---|
| Tensile strength at Break (MT/TD*) | ASTM D 882 | Mpa | 25/20 |
| Elongation at break (MT/TD*) | ASTM D 882 | % | 280/870 |
| Dart drop impact | ASTM D 1709 | g/F50 | 140 |
| Elmendorf tear strength (MT/TD*) | ASTM D 1922 | gF | -/160 |
| Haze | ASTM D 1003 | % | 9 |
| Gloss-45° Angle | ASTM D 2457 | % | 60 |
| Gloss-60° Angle | ASTM D 2457 | % | 90 |

*MT = Machine direction;
TD = Transversal direction.

Preferably, the outer layer 16 (preferably of recycled thermoplastic polymer or made of bio-based thermoplastic polymer) comprises at least one UV protection agent mixed with the thermoplastic polymer, preferably homogeneously. Preferably, the UV protection agent is mixed with said thermoplastic polymer of the outer layer 16 at any amount comprised from 0.1% to 15% by weight with respect to the total weight of the thermoplastic polymer, more preferably at an amount comprised from 0.5% to 10% by weight, even more preferably at an amount comprised from 0.8% to 5% by weight.

Preferably, the container body 40, or the lateral wall 8 and/or the bottom wall 12, could comprise or, alternatively, consist of the inner layer 14 comprising said compound material comprising the thermoplastic polymer, the first zeolite, the second zeolite, each zeolite comprising the antibacterial and/or bacteriostatic metal ions defined herein as essential, and the outer layer 16 (preferably made of recycled thermoplastic polymer or made of bio-based thermoplastic polymer) comprising the at least one UV-protective agent mixed with the thermoplastic polymer of the outer layer 16.

For example, the inner layer 14 and the outer layer could consist of the same type of thermoplastic polymer (for example PE, or ABS), or compatible polymers, wherein only the polymer of the inner layer 14 comprises or is loaded with the first and with the second zeolite.

In the present description, the expression "compatible" is used to indicate two polymers capable of joining or welding stably, when either one of them in an at least partially softened or molten is brought to contact with the other.

Optionally, the outer layer 16 could be joined to the inner layer 14 by means of an intermediate layer 48 (only schematically shown in FIG. 2B), for example with compatibilizing properties between the inner layer 14 and the outer layer 16. For example, this variant could prove advantageous if the two polymers used were mutually incompatible, and therefore with a tendency to separate in the absence of such an intermediate layer.

Preferably, the container body 40, or the lateral wall 8 and/or the bottom wall 12, could comprise the inner layer 14, one or more intermediate layers 48 and the outer layer 16, preferably at least one intermediate layer 48 being a gas and/or moisture barrier layer. More preferably, the gas and/or moisture barrier layer is an ethylene-vinyl alcohol (EVOH) copolymer layer. Even more preferably, the gas and/or moisture barrier layer (preferably the EVOH copolymer layer) could be bonded with the inner layer 14 by means of a first adhesive layer and with the outer layer 16 by means of a second adhesive layer.

The characteristics of the ethylene-vinyl alcohol copolymer layer can be designed based on a [ethylene units]: [vinyl alcohol unit] by mole ratio in said copolymer. Preferably, an amount of the ethylene units in said EVOH copolymer is comprised from 23% to 50% by moles, more preferably from 27% to 48% by moles, even more preferably from 32% to 44% by moles.

According to a particularly preferred embodiment, the container body 40 (or the lateral wall 8 and/or the bottom wall 12) could comprise (from the inside to the outside of the container):

(i) an inner layer 14 comprising said compound material comprising the thermoplastic polymer, the first zeolite, the second zeolite, each zeolite comprising the antibacterial and/or bacteriostatic metal ions defined herein as essential;
(ii) a first adhesive layer;
(iii) at least one intermediate layer 48 as a gas and/or moisture barrier layer, said gas and/or moisture barrier layer preferably being an ethylene-vinyl alcohol (EVOH) copolymer layer;
(iv) a second adhesive layer;
(v) an outer layer 16 made of recycled thermoplastic polymer, preferably recycled low-density polyethylene.

According to other embodiments, the tubular wall 8 and/or the bottom wall 12 could be obtained (with only one layer or with several layers) by means of any of the following techniques: extrusion, moulding, injection moulding, injection-blow moulding, extrusion blow moulding, injection-stretch-blow moulding, or extrusion-stretch-blow moulding.

In an embodiment, the sterile container 1 could comprise a dispensing element 18 communicating with the containment compartment 6 and connected to the container body 40, for example to the lateral wall 8 thereof.

In particular, the dispensing element 18 could be arranged at a second axial end 32 of the container body 40, opposite the first axial end 30.

Figure 4:
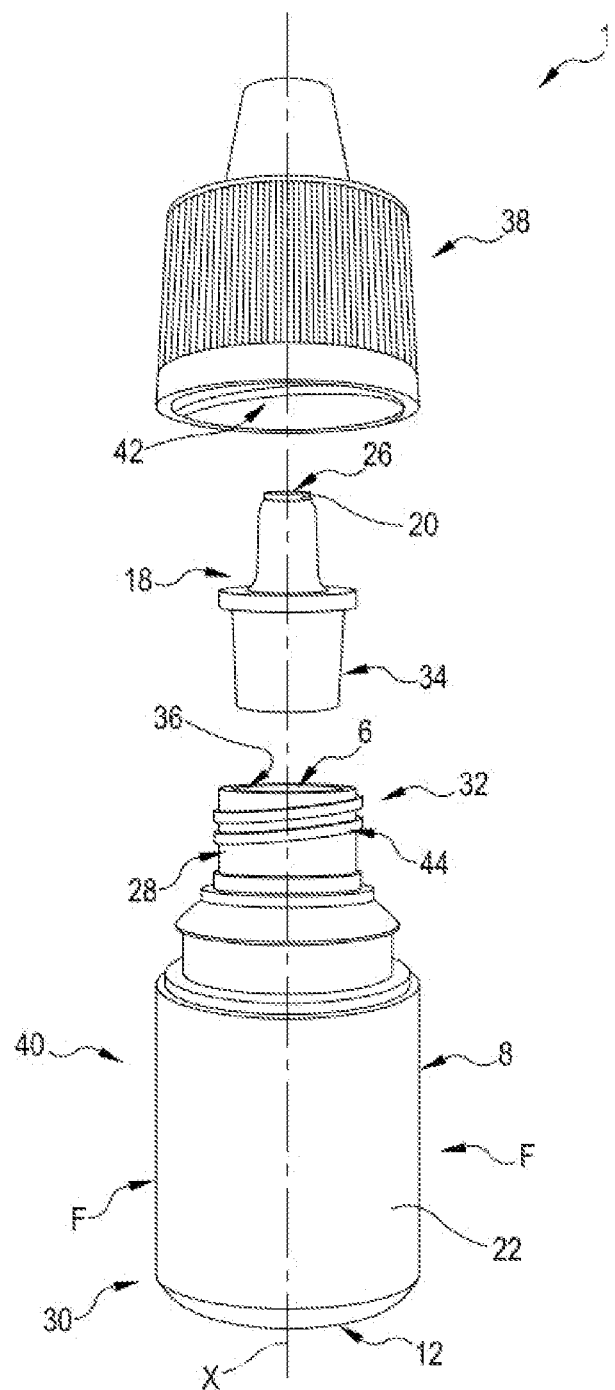
FIG. 4 shows a view with separated parts of a container, subject of the present invention, according to another possible embodiment.

According to different embodiments, the dispensing element 18 could be obtained as a single piece with the container body 40 or—as for example shown schematically in FIG. 4—it could consist of a piece mechanically separated from, and connected to, the container body 40 or to the lateral wall 8, for example with a shape or force coupling.

According to a variant, the dispensing element 18 could be connected to a neck or to a radial narrowing 28 of the container body 40.

According to a possible variant, the dispensing element 18 could comprise a first connection portion 34 connected to a second connection portion 36 of the container body 40. For example, the radial or radial narrowing 28 of the container body 40 could constitute at least part of the second connection portion 36.

According to a further variant, the first connection portion 34 and the second connection portion 36 could comprise complementary tubular portions, in particular mounted coaxially to each other, preferably sealingly.

By way of example, the first connection portion 34 of the dispensing element 18 could be sealingly inserted into the second connection portion 36 of the container body 40.

In the shown embodiments, the dispensing element 18 comprises or consists of a dropper element. Other embodiments of such element 18 are however possible.

The dispensing element 18 advantageously delimits at least one opening 26 for discharging the content from the containment compartment 6, through which said content can pass externally.

According to an advantageous variant, at least the lateral wall 8 of the container body 40 could be partly collapsible by an external force F, so as to reduce the volume of the containment compartment 6. In particular, this allows to force the contents of the containment compartment 6 through the dispensing element 18 or through the dropper element.

Figure 3:
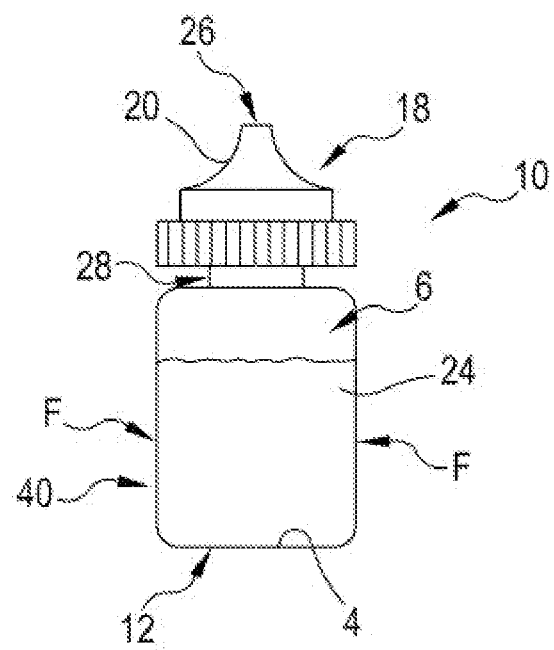
FIG. 3 shows a schematic lateral view of a sterile product, subject of the present invention, according to a possible embodiment.

More precisely, the external force F could be exerted by the fingers of a user, with the container in an inverted position, acting on the lateral wall 8 as schematised by at least one of the radial arrows in FIG. 3 or in FIG. 4.

According to a further advantageous variant, at least a part of an outer surface 20 of the dispensing element 18 comprises the compound material.

According to an even further advantageous variant, the dispensing element 18 mainly or wholly consists of the compound material.

Optionally, the sterile container 1 could comprise a closure element 38 releasably (and reversibly) connected to the container body 40, for example by means of complementary threads 42, 44 arranged at such element 38 and body 40.

According to an advantageous variant, the sterile container 1 could comprise one or more ion exchange elements 46, at least partially consisting of the compound material and protruding into the housing compartment 6, to increase a solid-liquid interface surface for the ion exchange at the first and at the second zeolite.

For example, at least one ion exchange element 46 could be obtained in the form of a strip 50 or in a tubular form.

In the tubular variant, at least one wall of the ion exchange element 46 could be traversed by one or more passages, for example at the discharge opening, so as not to prevent the contents from coming out from the containment compartment.

As far as the axial extension of the ion exchange element 46 is concerned, this length could be selected so that the element 46 can draw from the sterile aqueous solution at least partly, or mainly (at least as far as an initial/predefined or "factory" filling is of the container body is concerned).

According to an embodiment, one or more ion exchange elements 46 could be joined or obtained as a single piece with the dispensing element 18.

More precisely, at least one ion exchange element 46 could be connected to the first connection portion 34.

Advantageously, at least one ion exchange element 46 could be an axial extension of the dispensing element 18 or of the first connection portion 34 toward the bottom wall 4.

Figure 5:
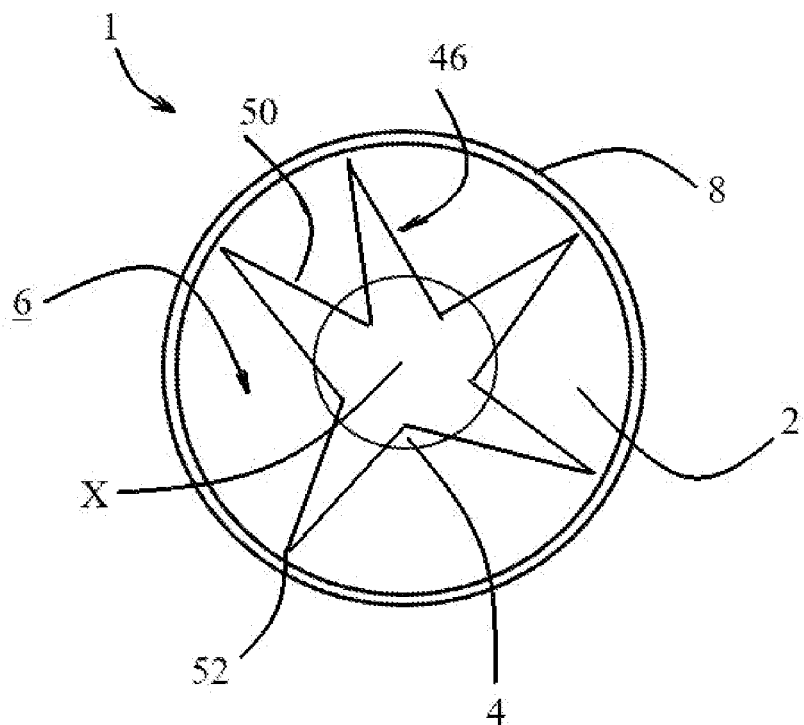
FIG. 5 and FIG. 6 show two plan views in orthogonal section of containers, subject of the present invention, according to even further embodiments.
Figure 6:
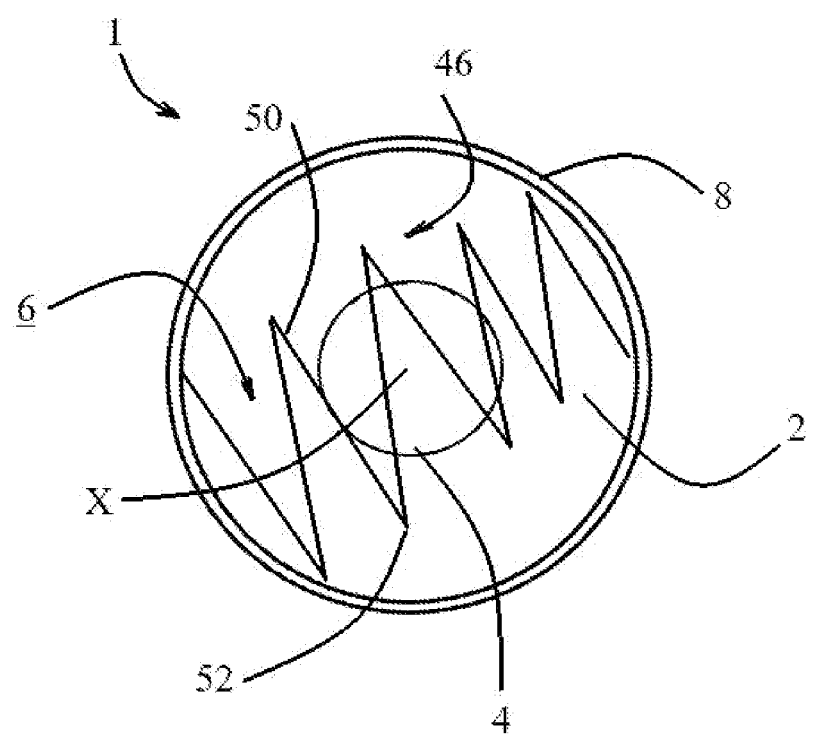

Preferably, the ion exchange element 46 could comprise a single strip 50 or a plurality of strips 50 oriented along a radial and/or axial direction (with respect to the main extension axis X) of the container body 40, or oriented in a direction axial and/or incident to a radial direction (with respect to the main extension axis X) of the container body 40. With reference to such embodiments, reference is made, for example, to FIG. 1, FIG. 5 and FIG. 6.

More preferably, at least one pair (or each pair) of said blades 50 could be joined at a common longitudinal edge 52, said edge extending along (for example parallel) the main extension axis X. Said joining at the longitudinal edge 52 could be obtained by means of a bent portion between said pair, or between each pair, of said strips 50. Said plurality of strips 50 could be loop-closed, as for example shown schematically in FIG. 5, around the main extension axis X, or it could be in the form of a bellows, as for example shown in FIG. 6, preferably said bellows being arranged with a diametrical orientation (relative to the main extension axis) in the containment compartment 6. In this configuration, the strips 50 are preferably arranged in an incident or orthogonal manner with respect to the radial direction.

The objectives outlined above are also attained by means of a compound material comprising a thermoplastic polymer, a first zeolite and a second zeolite homogeneously dispersed in the thermoplastic polymer, each of such zeolites having a micrometric particle size distribution and delimiting reticular voids in which bactericidal and/or bacteriostatic metal ions releasable from said zeolite are housed. The first zeolite comprises silver and copper metal ions, the second zeolite comprises silver and zinc metal ions. With regard to the preferred or advantageous characteristics of such material, reference is made to the description outlined above.

According to an embodiment, said compound material is in the form of semi-finished product, for example in the form of granule or pellet.

Furthermore, forming an object of the present invention is an ion exchange element 46 at least partially (for example: completely) made of said compound material, said ion exchange element being insertable into a container for housing a sterile product 10, for example for ophthalmic use.

Lastly, the objectives outlined above are attained by means of the sterile product 10 mentioned in the introduction, comprising a sterile aqueous solution 24 (or alternatively another preparation) containing ions of at least one alkaline metal (for example sodium ions and/or potassium ions) and the sterile container 1—according to any one of the embodiments illustrated above—housing the sterile aqueous solution 24 in the containment compartment 6.

By way of example, the sterile product 10 could comprise an ophthalmic pharmaceutical product, and/or an ophthalmic medical device.

It should be observed that the alkali metal ions—at contact with the first zeolite and with the second zeolite
 are configured to release the bactericidal and/or bacteriostatic metal ions in the sterile aqueous solution 24, by means of ion exchange.

Thus, the bactericidal and/or bacteriostatic metal ions are advantageously transferred to the sterile aqueous solution 24, where they also perform the fungicide function thereof.

It should also be observed that the ion exchange between the aforementioned ions will reach a balance after a predefined time, so that—upon achieving a determined equilibrium concentration of the silver, copper and zinc ions in the solution—no further release of bactericidal and/or bacteriostatic ions from zeolites will occur.

Optionally, the sterile aqueous solution 24 could contain glycerine and/or ethylenediaminetetraacetic acid (EDTA), for example in small amounts.

According to a particularly advantageous aspect of the invention, the efficacy of the antimicrobial preservation of the sterile aqueous solution 24 in the sterile container 1 complies with test 07/2011:50103 of European Pharmacopoeia 9.0, "5.1.3. Efficacy of antimicrobial preservation", in force at the date of priority of the present application.

More precisely, the sterile product 10 subject of the present invention allowed to achieve the most selective criterion "A" of the previous standard in some variants, and the criterion "B" according to other embodiments.

EXAMPLES

Example 1: Antibacterial and/or Bacteriostatic Efficacy Test for the Container Subject of the Present Invention Containing a Sorbitol Buffer Solution The tested container subject of the present invention ("PACTIVE") comprises a container body consisting of low-density polyethylene (LDPE), and containing 8% of a first zeolite comprising silver and copper metal ions and 8% of a second zeolite comprising silver and zinc metal ions. Said zeolites being homogeneously dispersed in the LDPE and they are arranged at inner surfaces which delimit a containment compartment of said container. The container was not irradiated before the test.

The sorbitol buffer solution used has the following composition: sorbitol 5.000 g; NaOH 0.1 N up to pH 7.2, purified water up to 100 ml. Said container was filled with 10 ml of the sorbitol buffer solution prepared as outlined above, said solution being first filtered with laminar flow through a 0.2 µm membrane.

The tests were conducted according to the European Pharmacopoeia, Ph. Eur. 5.1.3 (07/2011:50103) standard and the results obtained after predefined time intervals (6 hours, 24 hours, 7 days, 14 days, 28 days) are summarised in the following Table 1 for the *Staphylococcus aureus, Pseudomonas aeruginosa, Candida albicans, Aspergillus brasiliensis* bacteria, concisely identified in the first column.

(specified in Table 1), as concerns the four bacteria subject of test and as concerns the entire shelf-life. It should be observed that the 7-day value of *Aspergillus* brassiliensis is to be considered an anomalous value which is currently subject of investigation.

Example 2: Determination of Ag, Cu, Zn in a Phosphate-Buffered Saline Solution

A container of Example 1 was filled with 10 ml of phosphate buffered saline, subjected to a temperature of 60° C. for 10 days. The amounts of the elements transferred or released by said zeolites of the container in the solution are indicated in Table 2 below.

TABLE 2

| Element | µg container |
|---------|--------------|
| Ag      | <1.00        |
| Cu      | 7.00         |
| Zn      | 17.00        |

Example 3: Determination of Ag, Cu, Zn in a Sodium Chloride Saline Solution

A container of Example 1 was filled with 10 ml of sodium chloride solution (at 0.9% by weight with respect to the total weight of said solution) and subjected to a temperature of 60° C. for 10 days. The amounts of the elements transferred or released by said zeolites of the container in the solution are indicated in Table 3 below.

TABLE 3

| Element | µg container |
|---------|--------------|
| Ag      | 0.005        |
| Cu      | 0.003        |
| Zn      | 0.027        |

Table 2 and Table 3 above show that the quantities of the elements transferred or released by the zeolites strongly depend on the type of solution used in the test, not only as concerns the total amounts of ions released but also on the priority scale of the three ions considered in the various

TABLE 1

| SPECIES | | 6 h | 24 h | 7 d | 14 d | 28 d |
|---------|---|-----|------|-----|------|------|
| AUREUS | Criterion A | 2 Log | 3 Log | n.a. | n.a. | No recovery |
|  | Criterion B | n.a. | 1 Log | 3 Log | n.a. | No increases |
|  | PACTIVE | 2 Log | 4.05 Log | >5 Log | >5 Log | >5 Log |
| AERUGINOSA | Criterion A | 3 Log | 3 Log | n.a. | n.a. | No recovery |
|  | Criterion B | n.a. | 1 Log | 3 Log | n.a. | No increases |
|  | PACTIVE | 4.36 Log | >5 Log | >5 Log | >5 Log | >5 Log |
| ALBICANS | Criterion A | n.a. | n.a. | 2 Log | n.a. | No recovery |
|  | Criterion B | n.a. | n.a. | n.a. | 1 Log | No increases |
|  | PACTIVE | n.a. | n.a. | 2.86 Log | 2.89 Log | 2.97 Log |
| BRASILIENSIS | Criterion A | n.a. | n.a. | 2 Log | n.a. | No recovery |
|  | Criterion B | n.a. | n.a. | n.a. | 1 Log | No increases |
|  | PACTIVE | n.a. | n.a. | 0.71 Log* | 1.01 Log | 2.21 |

*to be verified

The activity assessment criteria are provided in terms of logarithmic reduction of viable microorganisms from the value obtained for inoculation.

Table 1 above shows that the "PACTIVE" container of the present invention meets both Criterion A and Criterion B solutions. In particular, in the presence of a sodium chloride solution (Table 3), the total amounts of the ions released are several orders of magnitude lower than the tests conducted in the presence of the phosphate buffered saline solution (Table 2).

With regard to the priority scales, Table 2 above shows that the exchange capacity of zinc, copper and silver decreases in this order, while—in sodium chloride saline solution—zinc always shows the greatest capacity while silver precedes copper in quantitative terms without prejudice to the fact that the slight difference could be due to an error in the analytical method.

The previous trends appear to be extremely advantageous in that:
1. The transfer of ions subdivided by permissible daily exposure (PDEs) is close to zero;
2. an open-hole sterile container shows levels of contamination of sterile contents at least comparable to the structurally more complex insulated containers (with closed-hole and/or without replenishment of air and/or with replenishment of controlled-air);
3. there are no limitations on the viscosity of the solution, of the liquid or of the preparation suitable for being contained in the containment compartment;
4. there are no limitations on the shape and/or size of the sterile container, hence the latter is suitable for any type of use;
5. protection against possible contamination is ensured up to the opening to discharge the content of the container, both internally and on the outer surfaces of the container.

Innovatively, the present invention allows to overcome the drawbacks of the prior art.

More precisely, the inventors of the present invention surprisingly found that the solutions outlined above allow to obtain an improved fungicidal action with respect to the prior art.

Advantageously, in the present invention the silver ion has a greater homogeneity of distribution in the compound material, given that it is present on both zeolites, and therefore distributed in the material in an extremely uniform manner.

Advantageously, in the present invention the percentage of silver ions can be selected at a lower amount (slight or large) with respect to the other ions. Thus, the amount of silver ions may be generally relatively low, at least with respect to the other copper and zinc ions.

Advantageously, the inventors of the present invention found that the percentage of zeolites in the compound material preferably should not exceed a maximum threshold (for example 8.5% by weight), since a further increase only causes an increase in production cost, and it does not lead to a corresponding increased effectiveness.

Advantageously, the present invention is suitable for being implemented through known production techniques, without generating investment costs in new plants or equipment.

Advantageously, in the present invention the production cost of the container can be modulated using a suitable thickness of the layers, for example by specifically reducing the thickness of the layer containing the zeolites.

Advantageously, in the present invention an effective antibacterial and/or bacteriostatic action is carried out also at the outer surfaces of the container, where small amounts of solution easily contaminated from the outside could stop. This characteristic confers the container subject of the present invention properties in line with a recent standard introduced—in October 2018—by the European Medicines Agency (EMA), "Quality of medications questions and answers: Part 2"), according to which qualitative data are required to demonstrate the stability of eye drops in multi-dose containers for the entire in-use shelf-life of said drops (maximum shelf life: 28 days unless a longer period is justifiable).

More precisely, over the entire in-use shelf-life of said drops, a suitable container must prevent contamination of the sterile contents, and minimize microbial growth on the wettable inner and outer surfaces of the dropper element (biofilm formation). Said suitability must also be considered in the presence of damaged or improperly used containers, in various orientations of the container, so as to determine a possible influence of the orientation of the container on the stability of the drops. The micro-organisms subject of testing were selected according to the European Pharmacopoeia (EP 5.1.3, 07/2011:50103) requirements, in the presence of suitable positive or negative controls to demonstrate the antibacterial and/or bacteriostatic efficacy.

Therefore, in conclusion, the present container also proved to comply with the aforementioned EMA standard.

According to a further advantageous aspect, the present container at least partly obtained using the compound material was specially designed so that a possible proliferation from contamination is kept under control. More precisely, the conformation subject of discussion allows to exercise such control both internally, where the content resides, and externally, where the content could reach for example following repeated dispensing.

Advantageously, since the inner surfaces have an area limited by the internal volume of the containment compartment, in the present invention it is possible to provide an additional surface so that a greater amount of antibacterial and/or bacteriostatic metal ions can be released.

Advantageously, in the present invention the fungicidal efficacy can be further increased through small amounts of additives in solution.

Advantageously, the sterile product of the present invention can be opened, used and re-closed repeatedly, keeping the proliferation of possible contaminations, even if caused by external factors, under control.

Advantageously, in the present invention it is suspected that the presence of small amounts of metal ions in the sterile aqueous solution may have favourable repercussions in the treatment of certain diseases.

Advantageously, in the present invention the presence of the specified zeolites entails unexpected mechanical advantages of the container, for example in terms of ease of use of the container and/or compression of the lateral wall.

Advantageously, the container subject of the present invention allows to obtain a markedly higher ion exchange surface with respect to conventional containers, regarding which the exchange surface is solely limited to the surfaces of the container.

Advantageously, the compound material subject of the present invention can be used to obtain: in a first embodiment, only a container or a part thereof (for example a part or all of the inner surfaces) or, in a second embodiment, only one ion exchange element or a part thereof (for example to be used with a container of the conventional type, without the compound material of the present invention) or, in a third embodiment, to obtain both the container and the ion exchange element, or at least a part of both.

With respect to the embodiments of the of the aforementioned compound material, container and product, a man skilled in the art may replace or modify the described characteristics according to the contingencies. These variants are also to be considered included in the scope of protection as outlined in the claims that follow.

Furthermore, it should be observed that any embodiment may be implemented independently from the other embodiments described.

LIST OF REFERENCE NUMBERS 1 sterile container
2 inner surface, in particular of the lateral wall
4 inner surface, in particular of the bottom wall
6 containment compartment
8 lateral wall
10 sterile product
12 bottom wall
14 inner layer of the lateral wall and/or of the bottom wall
16 outer layer of the lateral wall and/or of the bottom wall
18 dispensing element or dropper element
20 outer surface of the dispensing element
22 outer surface of the container body
24 sterile aqueous solution
26 discharge opening
28 neck or radial narrowing
30 first axial end
32 second axial end
34 first connection portion
36 second connection portion
38 closing element
40 container body
42 thread, for example internal thread
44 thread, for example external thread
46 ion exchange element
48 intermediate layer of the lateral wall and/or of the bottom wall
50 strip
52 longitudinal edge
F external force
X main extension axis

The invention claimed is:

1. A sterile container (1) comprising a container body (40) having inner surfaces (2, 4) delimiting a containment compartment (6), wherein at least part of said surfaces (2, 4) is made of a compound material comprising a thermoplastic polymer, a first zeolite and a second zeolite homogeneously dispersed in the thermoplastic polymer, each of said zeolites having a micrometric particle size distribution and delimiting reticular voids in which bactericidal and/or bacteriostatic metal ions releasable from said zeolite are housed;
wherein:
the first and second zeolites are different,
the compound material comprises—per 100 grams of thermoplastic polymer—an amount of first zeolite equal to or greater than 5.5% by weight (% wt), and an amount of second zeolite equal to or greater than 5.5% by weight (% wt),
the first zeolite consists of: (i) sodalite, mordenite, analcite, clinoptilolite, chabazite, erionite, zeolite A, zeolite X, zeolite Y, zeolite T, or any mixture thereof, and (ii) silver and copper metal ions,
the second zeolite consists of (i) sodalite, mordenite, analcite, clinoptilolite, chabazite, erionite, zeolite A, zeolite X, zeolite Y, zeolite T, or any mixture thereof, and (ii) silver and zinc metal ions, and
the following formula is valid:

$$0.05 < (Ag1+Ag2)/(Cu1+Zn2) < 0.8$$

wherein:
Ag1 is the percentage by weight (% wt) of the silver ions with respect to the weight of the first zeolite;
Ag2 is the percentage by weight (% wt) of the silver ions with respect to the weight of the second zeolite;
Cu1 is the percentage by weight (% wt) of the copper ions with respect to the weight of the first zeolite; and
Zn2 is the percentage by weight (% wt) of the zinc ions with respect to the weight of the second zeolite.

2. The sterile container according to claim 1, wherein the percentage by weight of the silver ions with respect to the weight of the first zeolite (Ag1) is comprised in the range from 2-5% (% wt), and wherein the percentage by weight of the silver ions with respect to the weight of the second zeolite (Ag2) is comprised in the range from 4.3-5.5% (% wt).

3. The sterile container according to claim 1, wherein the percentage by weight of the copper ions with respect to the weight of the first zeolite (Cu1) is comprised in the range from 4-7% (% wt), and wherein the weight percentage of the zinc ions with respect to the weight of the second zeolite (Zn2) is comprised in the range from 12-16% (% wt).

4. The sterile container according to claim 1, wherein the thermoplastic polymer comprises or consists of high density or low-density polyethylene.

5. The sterile container according to the claim 1, wherein the container body (40) comprises an inner layer (14) comprising, or consisting of, the compound material, and at least one outer layer (16) free of zeolites and free of bactericidal and/or bacteriostatic metal ions, joined to the inner layer (14) as a single piece by co-extrusion, co-moulding, co-injection or over-moulding.

6. The sterile container according to claim 1, wherein the container body (40) comprises—from the inside to the outside:
(i) an inner layer (14) comprising said compound material;
(ii) a first adhesive layer;
(iii) at least one intermediate layer (48) as a gas and/or moisture barrier layer, said gas and/or moisture barrier layer being a layer of an ethylene-vinyl alcohol (EVOH) copolymer;
(iv) a second adhesive layer; and
(v) an outer layer (16) made of recycled thermoplastic polymer.

7. The sterile container according to claim 1, comprising a dispensing element (18) in communication with the containment compartment (6) and connected to the container body (40), at least part of an outer surface (20) of said element (18) comprising said compound material.

8. The sterile container according to claim 7, comprising one or more ion exchange elements (46), at least partially made of the compound material and projecting into the housing compartment (6), so as to increase a solid-liquid interface surface for ion exchange at the first and second zeolite, said one or more ion exchange elements (46) being joined or made as a single piece with the dispensing element (18).

9. The sterile container according to claim 1, wherein said container (1) is a tray or container for contact lenses, a bottle, or a phial.

10. The sterile container according to claim 1, wherein:
said container—filled with 10 ml of phosphate-buffered saline solution and subjected to a temperature of 60° C. for 10 days—releases bactericidal and/or bacteriostatic metal ions from said zeolites at the following amounts: silver <1.00 μg, copper 7.00 μg, zinc 17.00 μg; and/or
said container—filled with 10 ml of a sodium chloride solution (0.9% by weight with respect to the total weight of said solution) and subjected to a temperature of 60° C. for 10 days—releases bactericidal and/or bacteriostatic metal ions from said zeolites at the following amounts: silver 0.005 µg, copper 0.005 µg, zinc 0.027 µg.

11. A sterile product (10), comprising:
a) a sterile aqueous solution (24) containing ions of at least one alkali metal;
b) the sterile container (1) according to claim 1 housing the sterile aqueous solution (24) in the containment compartment (6);
wherein the alkali metal ions—at contact with the first zeolite and with the second zeolite—are configured to release the bactericidal and/or bacteriostatic metal ions in said sterile aqueous solution (24) by means of ion exchange.

12. The sterile container according to claim 1, wherein the sterile aqueous solution (24) contains glycerine and/or ethylenediaminetetraacetic acid (EDTA).

13. The sterile product according to claim 11, wherein the sterile aqueous solution (24) in said container (1):
a) reduces the viability of an initial inoculum of *Staphylococcus aureus* greater than or equal to 1 Log at 6 hours after inoculation, greater than or equal to 3 Log at 24 hours after inoculation, and prevents recovery or increase in viability of the *Staphylococcus aureus* inoculum at 28 days after inoculation;
b) reduces the viability of an initial inoculum of *Pseudomonas aeruginosa* greater than or equal to 2 Log at 6 hours after inoculation, greater than or equal to 3 Log at 24 hours after inoculation, and prevents recovery or increase in viability of the *Pseudomonas aeruginosa* inoculum at 28 days after inoculation;
c) reduces the viability of an initial inoculum of *Candida albicans* greater than or equal to 2 Log at 7 days after inoculation, and prevents recovery or increase in viability of the *Candida albicans* inoculum at 28 days after inoculation; and
d) reduces the viability of an initial inoculum of *Aspergillus brasiliensis* greater than or equal to 2 Log at 7 days after inoculation, and prevents recovery or increase in viability of the *Aspergillus brasiliensis* inoculum at 28 days after inoculation.

* * * * *